United States Patent [19]

Berman

[11] Patent Number: 5,779,662
[45] Date of Patent: Jul. 14, 1998

[54] LAPAROSCOPIC TISSUE RESECTION SYSTEM

[75] Inventor: Phillip J. Berman, St. Petersburg, Fla.

[73] Assignee: Linvatec Corporation, Largo, Fla.

[21] Appl. No.: 650,362

[22] Filed: May 20, 1996

[51] Int. Cl.$^6$ .................................. A61M 1/00
[52] U.S. Cl. .......................... 604/22; 604/23; 604/26; 604/28; 604/35
[58] Field of Search ................ 604/22, 23, 26, 604/27, 35

[56] References Cited

U.S. PATENT DOCUMENTS

| | | |
|---|---|---|
| 4,167,943 | 9/1979 | Banko . |
| 4,324,243 | 4/1982 | Helgott et al. ........... 604/22 |
| 4,428,748 | 1/1984 | Peyman et al. .......... 604/22 |
| 4,650,461 | 3/1987 | Woods ...................... 604/28 |
| 4,662,371 | 5/1987 | Whipple et al. .......... 604/22 |
| 4,678,459 | 7/1987 | Onik et al. ............... 604/22 |
| 5,300,021 | 4/1994 | Wuchinich ................ 604/22 |
| 5,354,291 | 10/1994 | Bales et al. .............. 604/22 |
| 5,382,229 | 1/1995 | Grabenkort et al. . |
| 5,456,689 | 10/1995 | Kresch et al. ........... 604/22 |

*Primary Examiner*—Gary Jackson
*Attorney, Agent, or Firm*—Gene Warzecha

[57] ABSTRACT

A powered tissue resection system for use during endoscopic surgical procedures in which a body cavity is filled with a gas medium to maintain pneumoperitoneum. A powered tissue resection device is utilized to simultaneously resect and aspirate tissue from the surgical work site within the gas-filled body cavity. Along with the aspirated tissue a portion of the ambient fluid medium is aspirated. A separating means is provided to separate the resected tissue and other debris from the fluid medium, generally carbon dioxide, and return the latter to the body cavity to maintain pneumoperitoneum.

6 Claims, 5 Drawing Sheets

LAPAROSCOPIC TISSUE RESECTION SYSTEM

BACKGROUND OF THE INVENTION

1. Field of the invention

The invention relates to powered surgical tissue resection devices. More particularly, the invention relates to powered tissue resection devices for use in fluid filled cavities of the body. Still more particularly, the invention relates to powered tissue resection devices for use in laparoscopic OR thoracoscopic surgical procedures in which a body cavity is filled with a gaseous fluid medium.

2. Description of the Prior Art

Powered tissue resection is common in both open and some closed surgical procedures, the latter being generally referred to as arthroscopic or endoscopic surgery. The goal of the present invention is to provide powered tissue resection devices suitable for laparoscopic or thoracoscopic procedures in which a body cavity is pressurized with a gaseous medium. The terms "laparoscopic" and "endoscopic" may be used interchangeably herein and are intended to encompass arthroscopic, endoscopic, laparoscopic, hysteroscopic, thoracoscopic or any other similar closed surgical procedures performed with elongated instruments inserted through small, natural or artificially created openings or portals in the body. The instruments may be used in conjunction with an elongated camera which enables the surgeon to view the work site during the procedure.

While different endoscopic procedures obviously require instruments particularly adapted for the procedure, there is a common need to remove resected tissue. In laparoscopic procedures, tissue is resected with manual instruments which require the resected tissue to be manually removed. In some instances, an instrument may be used to take a bite of tissue and the instrument must then be withdrawn from the body to dispose of the tissue and then reinserted to repeat the process. Powered tissue resection would be preferable if, for example, arthroscopic-type instruments could be adapted for laparoscopic used. For example, in arthroscopic procedures performed on knee or shoulder joints, the joint is expanded with a fluid medium in order to not only provide distension but to enhance visualization by removing resected tissue and other debris from within the joint. Powered tissue resection devices used in such arthroscopic procedures, sometimes called shavers, are often in the form of an elongated, hollow inner tubular member situated to cyclically move (e.g. rotatably) within an elongated outer tubular member. The inner member is provided with a cutting device at its distal end and the outer tubular member is provided with a window or other opening enabling the cutting device of the inner member to resect desired tissue presented through the outer window. The resected tissue would remain suspended in the fluid, thereby clouding and obscuring the field of view, but for a vacuum applied to the interior of the inner member to aspirate the resected tissue from the joint. Since such aspiration necessarily removes ambient fluid as well, continual fluid flow through the joint is required to maintain a clean, debris-free field of view.

As the procedure continues, additional fluid must flow into the joint to replace the removed fluid and maintain the desired fluid pressure and distension. While the fluid is usually drained away, as described in U.S. Pat. 5,382,229 (Grabenkort et al.) the fluid normally used in an arthroscopic procedure may be recirculated through filters in order to minimize the volume of fluid required for the procedure.

Known laparoscopic and other endoscopic procedures have been unsuitable for adaptation to the aforementioned type of arthroscopic procedure. For example, in laparoscopic procedures, a patient's abdomen is pressurized with a gas such as carbon dioxide ($CO_2$) in order to distend the abdomen sufficiently to produce an adequate working space within the body cavity for laparoscopes and other elongated instruments inserted through several portals in the abdomen. The pressurization is achieved by an insufflation device sometimes referred to as a laparoflator which continues pumping $CO_2$ at the desired rate to maintain the desired pressure and replace the amount of gas lost during the procedure, for example, by leakage through the portals, etc. Laparoscopic procedures utilize the $CO_2$ primarily to create a working space and there is, therefore, no need to maintain fluid flow to continually clean the field of view. Tissue resection during laparoscopic procedures is done manually or by ablation, unlike the powered resection of arthroscopic procedures, because of the need to maintain a sufficient pneumoperitoneum to preserve visualization and working space. Resected tissue and debris is either manually removed directly or is aspirated out intermittently via a separate suction device which may or may not be a part of a combined irrigation/aspiration instrument. Such suction devices remove relatively little ambient gas which is easily replaced by the insufflating equipment. Use of a powered tissue resection device such as those used during arthroscopic procedures would remove significantly more gas from around the laparoscopic work site than the intermittently activated irrigation/aspiration instruments, thus depressurizing the cavity and causing loss of pneumoperitoneum. Also, loss of pneumoperitoneum while suctioning is far less dangerous than loss during resection.

It is accordingly an object of this invention to produce a powered tissue resection system for use in laparoscopic and thoracoscopic surgical procedures.

It is another object of this invention to produce a powered tissue resection device in which resected tissue is aspirated through the device along with a portion of the fluid medium within the body cavity in which the procedure is performed, the fluid then being returned to the work site to maintain pressure at the desired level.

It is yet another object of this invention to produce a powered tissue resection device in which the aspirated fluid medium is recirculated into the body cavity in which the surgical procedure is being performed.

It is also an object of this invention to produce a powered tissue resection device which is self-contained and adapted to be usable in any fluid-filled body cavity to maintain fluid pressure within the cavity during resection.

It is still another object of this invention to produce a powered tissue resection device suitable for tissue resection and pressure maintenance during laparoscopic and other procedures performed endoscopically in a gas-filled body cavity.

SUMMARY OF THE INVENTION

These and other objects of this invention are achieved by the preferred embodiment disclosed herein which is a tissue resection system for use in an endoscopic surgical procedure conducted in a closed body cavity filled with a pressurizing gas. The system comprises a cutting means for resecting tissue, an aspiration means for aspirating the resected tissue and gas from the cavity and a separating means for separating the resected tissue from the gas to produce reusable gas. The system further comprises a recirculating means for returning the reusable gas to the cavity.

Another aspect of this invention is a method of endoscopically resecting tissue in a gas filled body cavity. The method comprises the steps of pressurizing the body cavity with gas and maintaining the gas at a predetermined pressure within the body cavity. The method further comprises inserting into the body cavity a cutting means for resecting tissue, the cutting means having an aspirating lumen for aspirating resected tissue and gas, resecting selected tissue and then aspirating the resected tissue along with the ambient gas. Finally, the method comprises separating the resected tissue and gas to produce reusable gas and returning the reusable gas to the body cavity to replace the gas that was aspirated.

DESCRIPTION OF THE PREFERRED EMBODIMENT

Figure 1:
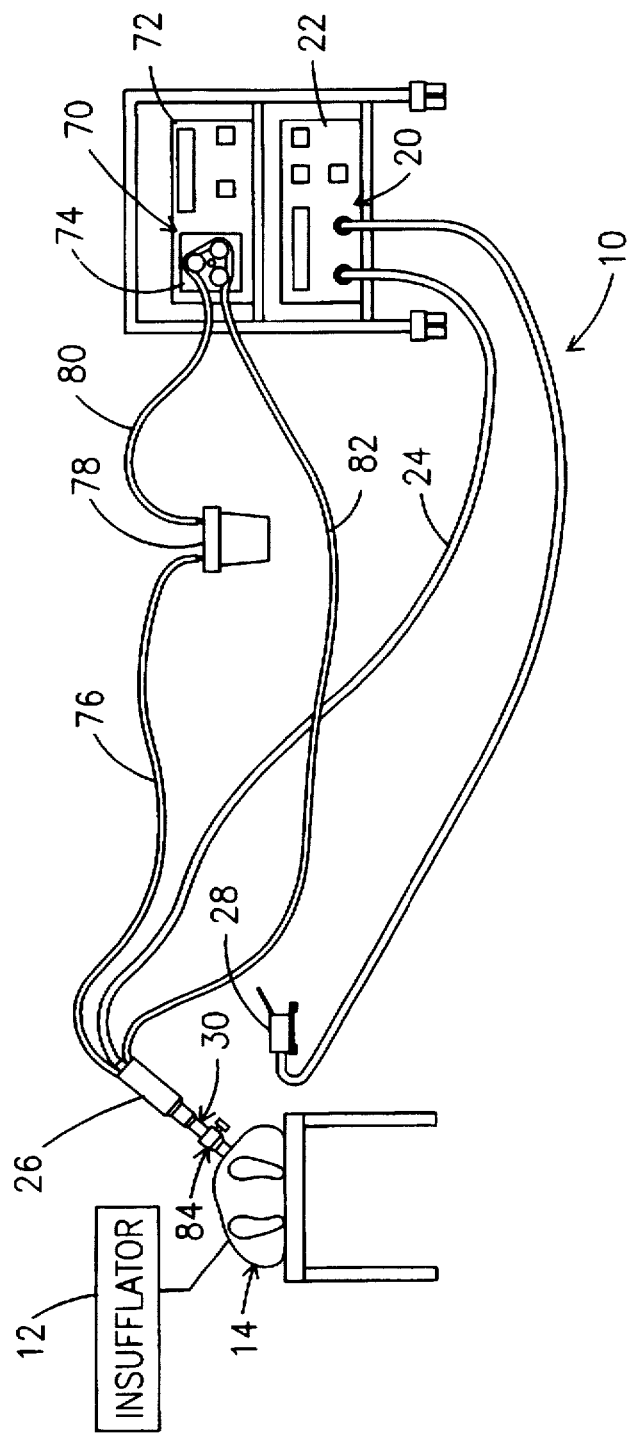
FIG. 1 is a diagrammatic representation of a powered laparoscopic tissue resection system constructed in accordance with the principles of this invention.

A diagrammatic representation of a laparoscopic tissue resection system 10 is shown in FIG. 1. System 10 operates in conjunction with a conventional insufflator 12 which provides pressurizing fluid to a patient 14 in a conventional manner. While the preferred embodiment utilizes $CO_2$, it will be understood that a suitable fluid medium other than $CO_2$ could also be used within the scope of this invention.

Figure 2:
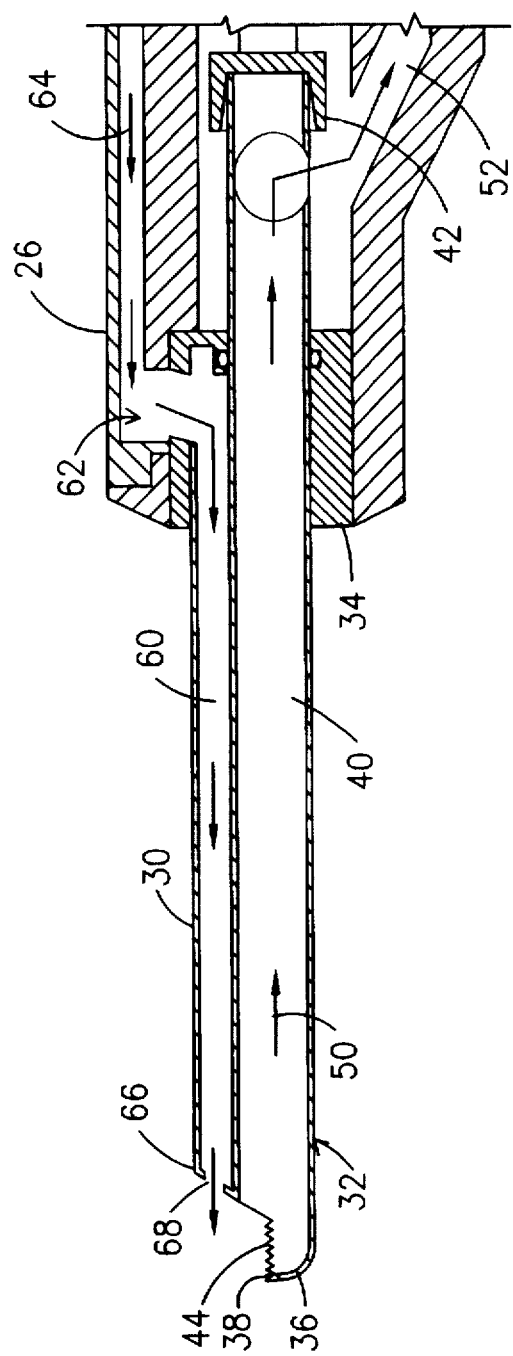
FIG. 2 is an exploded cross-sectional view of the distal portion of the handpiece shown in the system of FIG. 1.

System 10 comprises a powered resection system 20 further comprising a drive console 22 connected by an electrical cable 24 to a handpiece 26. The handpiece includes a rotatable motor (not shown) which may be controlled by a foot switch 28 or by switches directly located on the handpiece (not shown). As best seen in FIG. 2, handpiece 26 is adapted to receive a laparoscopic shaver blade assembly 30 which is preferably disposable and selectively attachable to the distal end of handpiece 26. While in an alternate embodiment handpiece 26 and shaver 30 may be conventional, single-lumen arthroscopic-type components, in the preferred embodiment shown in FIGS. 1 and 2, shaver 30 is a dual-lumen device comprising an elongated hollow outer tube 32 having a proximal end 34 attached to the distal end of handpiece 26 and a distal end 36 provided with a window opening 38. An elongated hollow inner tube 40 is rotatably received within the interior of outer tube 32 such that its proximal end 42 is detachably secured to a rotating drive within the handpiece (not shown) and its distal end 44 is provided with a cutting edge. The hollow interior 50 of the inner member is one lumen and is joined to an aspirating channel 52 within the handpiece which, as will be understood below, is connected to a vacuum source. Shaver 30 also comprises a gas return channel 60—the second lumen—having a proximal end 62 joined to a channel 64 within the handpiece and a distal end 66 having an opening 68. In the preferred embodiment, gas return channel 60 is formed as an integral part of outer tube 32 and handpiece 26 is provided with both inflow and outflow channels. The extra gas inflow channels in the handpiece and the shaver blade assembly distinguish the laparoscopic shaver system disclosed herein from a conventional arthroscopic shaver system.

Laparoscopic tissue resection system 10 also comprises a pressure maintenance system 70 which has a pump console 72 for driving and controlling a peristaltic pump 74. Pump 74 is attached to handpiece 26 via a gas outflow line 76 joined at its distal end to aspiration channel 52 within the handpiece. The proximal end of line 76 is connected to a suction canister and the output side of the suction canister is connected via an inflow line 80 to the rollers of the peristaltic pump. The other end of line 80 continues beyond the rollers and becomes inflow line 82 connected to the gas inflow channel 64 within handpiece 26. It will be understood that suction canister 78 retains any tissue debris carried by the gas aspirated from the body while permitting the gas to circulate through the pump tubing. A filter (not shown) may be included, if necessary, to reduce any particulate matter in the gas although, since there is no return to the insufflator there is little or no need to filter the gas prior to its return (depending upon the suction canister design and operation).

Figure 3:
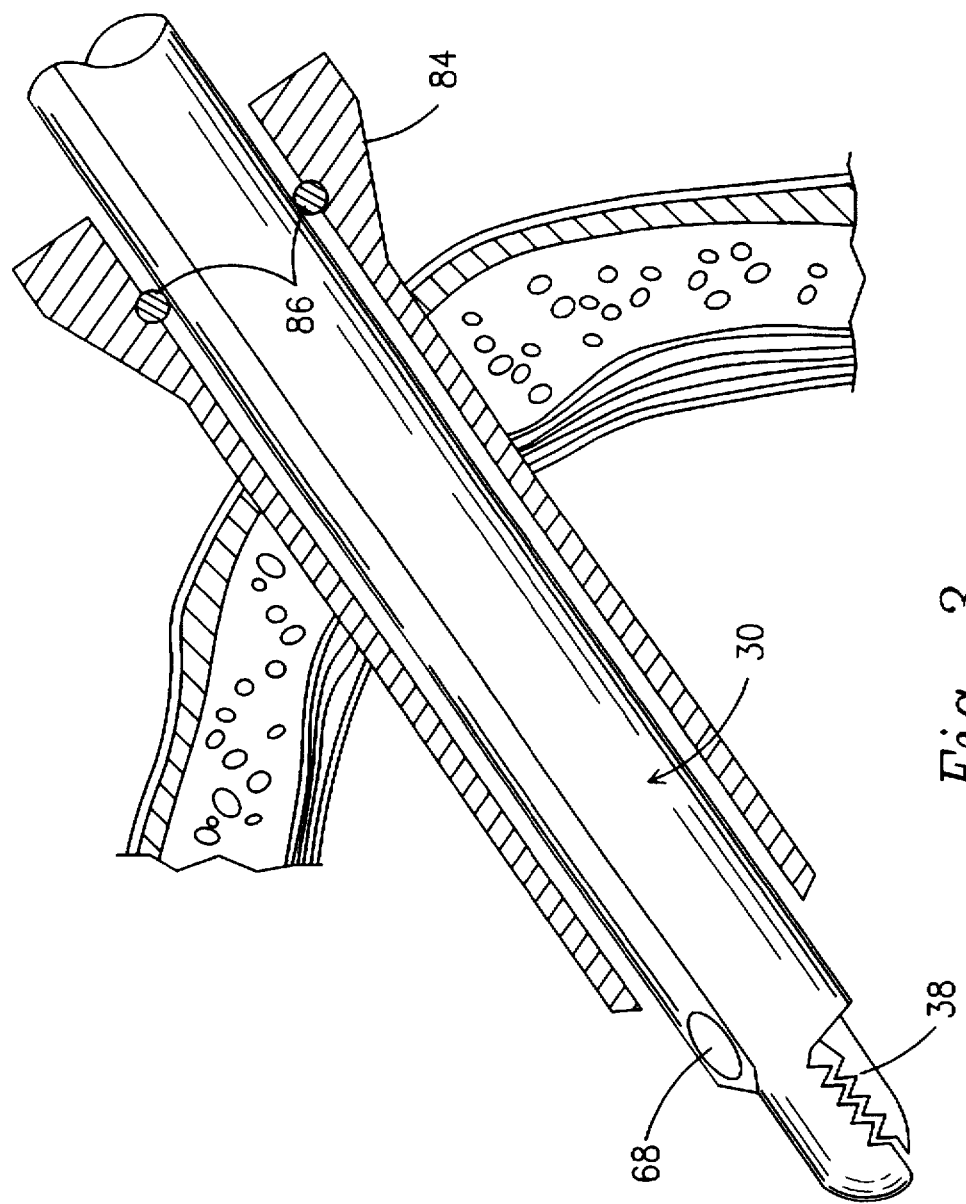
FIG. 3 is a diagrammatic cross-sectional view of the distal portion of the shaver of FIG. 2 within a cannula.

The laparoscopic shaver assembly 30 generally passes through a cannula 84 which serves as the entryway through a body portal. As best seen in FIG. 3, in the preferred embodiment cannula 84 has an annular seal 86 at its proximal end and simply provides a passageway for shaver 30. While in this embodiment the gas inlet return back into the body cavity is via opening 68 at the distal end of shaver 30, the alternate embodiment described below with respect to FIGS. 4 and 5 actually utilizes the body of the cannula as the gas return line. One advantage of system 10 is that a conventional cannula may be used since the remaining components comprise a self-contained system having all of the elements needed to recirculate the gas to maintain pressure in the body cavity.

Figure 4:
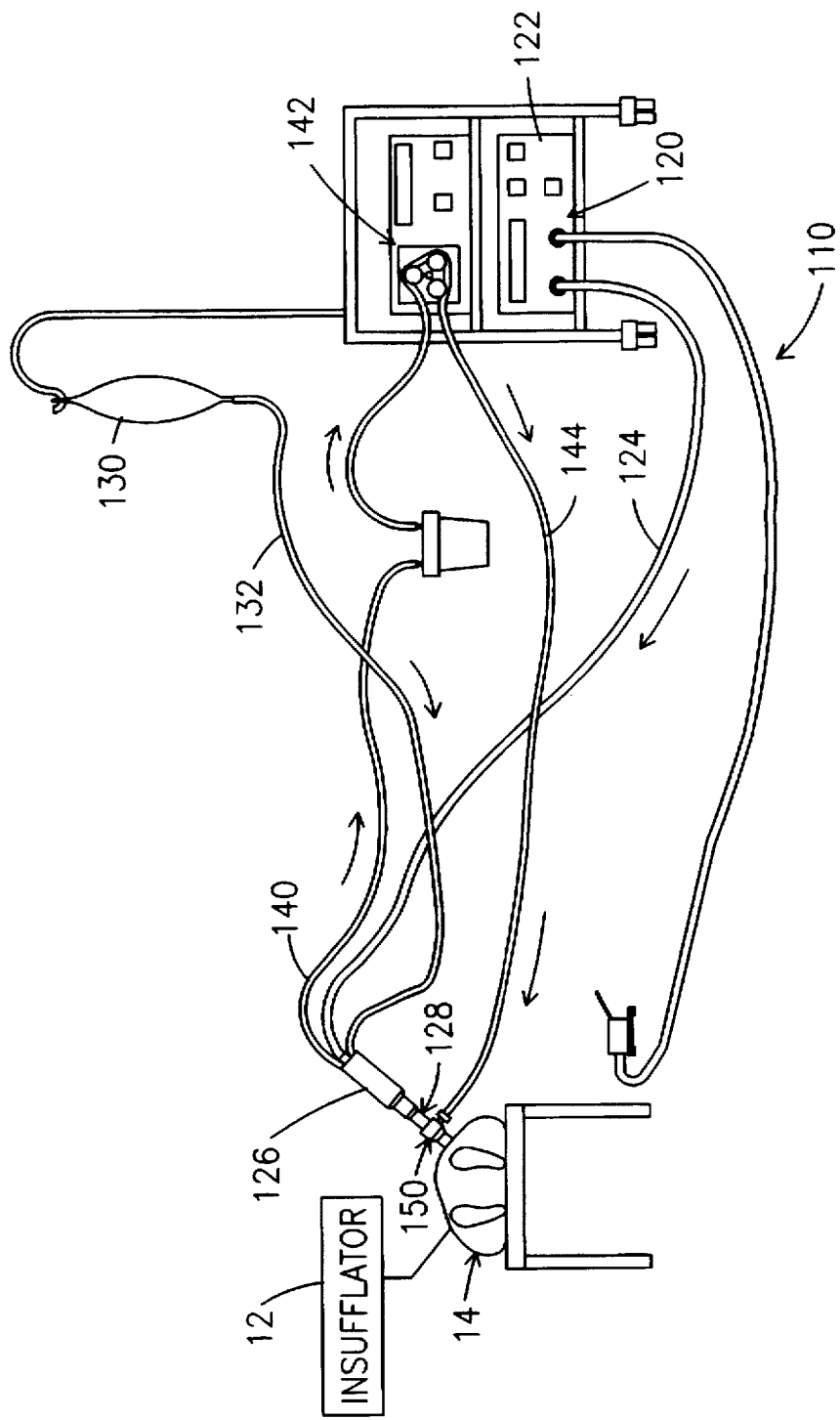
FIG. 4 is an alternative embodiment of a powered laparoscopic tissue resection system constructed in accordance with the principles of this invention.
Figure 5:
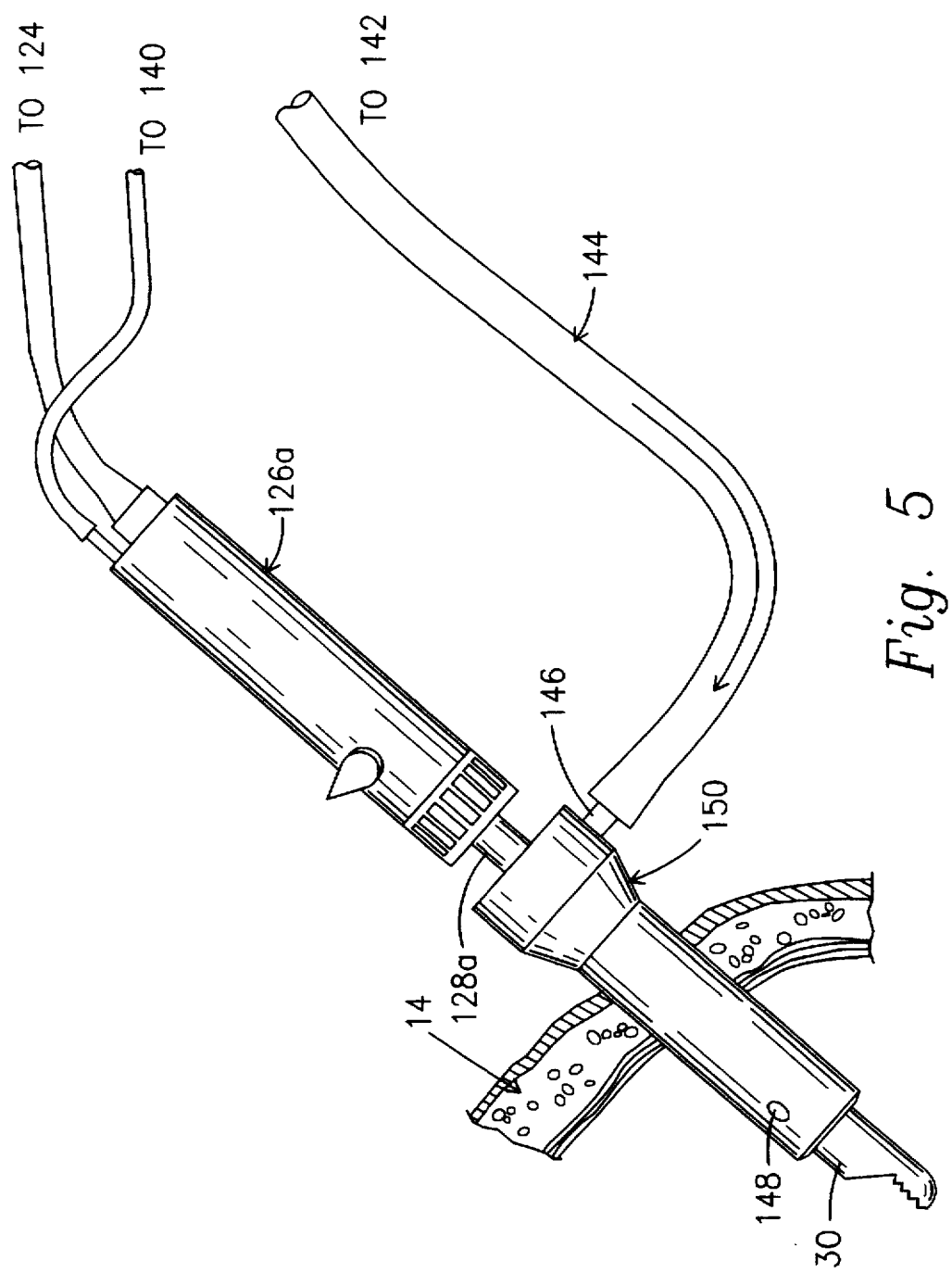
FIG. 5 is an exploded view of a portion of the system shown in FIG. 4.

The alternate embodiment shown in FIG. 4 is a laparoscopic tissue resection system 100 which is in many respects identical to system 10 shown in FIG. 1. Thus, a powered resection system 120 having a console 122, an electric cable 124 and handpiece 126 is utilized to provide powered resection. The shaver blade assembly 128 attached to the handpiece is identical to the dual lumen structure of shaver 30 although the gas inflow channel which was used in the shaver 30 for returning gas to the body cavity may be connected via handpiece 128 to an optional irrigation fluid source 130 joined to the inflow channel via line 132. A surgeon could utilize this irrigation fluid either continually or selectively (if controlled by a valve, not shown) to clean the resection site during the procedure. The spent irrigating fluid and the tissue debris and gas within the body cavity would then be aspirated through the handpiece via suction line 140 to a pump 142 as in the previous embodiment. In this embodiment, however, the return line 144 from the pump is connected directly to the input port 146 of inflow cannula 150, best seen in FIG. 5. Port 146 is in fluid communication with an outlet port 148 at the distal end of the cannula (downstream from any seal between the cannula and the blade assembly). The use of inflow cannula 150 enables system 100 to utilize a dual-lumen laparoscopic shaver blade assembly 128 and handpiece 126 or a conventional single-lumen arthroscopic shaver blade assembly 128a and handpiece 126a. Since conventional arthroscopic type shaver blades and handpieces do not normally have a separate gas inflow channel, it will be understood that in such a configuration, handpiece 126a and shaver blade assembly 128a would not enable use of the optional irrigation fluid via line 132. It will also be understood that a dual-lumen shaver blade assembly may be created by modifying a single-lumen assembly to utilize the annular space between the inner and outer members as one of the lumens.

as more fully described in a co-pending application assigned to the assignee hereof and incorporated by reference herein.

A peristaltic pump has the advantage of facilitating the control of the volume of gas removed from the body cavity. Thus, the control system of the pump can control the pump speed to provide the desired vacuum. The volume of gas removed from the suction line is simply transferred to the inflow line thus minimizing the change in pressure in the body cavity. Internal communications between the pump and the handpiece drive console adjusts the speed of the pump accordingly. Increased speed of the shaver blade will resect tissue at a faster rate than a slower speed and will result in increased suction on the resected tissue, thus requiring faster pump operation.

It will be understood that numerous modifications and improvements may be made to the preferred embodiment of the invention disclosed herein without departing from the spirit and scope thereof.

What is claimed is:

1. A tissue resection system for use in an endoscopic surgical procedure conducted in a closed body cavity having gas therein, said gas maintained at a predetermined pressure, said system comprising:

a cutting means for resecting tissue in said body cavity;

an aspiration means for aspirating resected tissue and gas from said cavity;

separating means for separating resected tissue from gas to produce reusable gas;

recirculating means for returning said reusable gas to said cavity.

2. A tissue resection system according to claim 1 wherein said cutting means comprises:

an elongated tubular outer member having a proximal end and a distal end with window;

an elongated tubular inner member adapted for cyclical movement in said outer member, said inner member having a proximal end and a distal end with a cutting member juxtaposed adjacent to said window.

3. A tissue resection system according to claim 2 wherein said cutting means further comprises:

first channel means to pass gas therethrough into said body cavity; and second channel means serving as said aspiration means for passing gas and/or resected tissue from said body cavity.

4. A tissue resection system according to claim 3 wherein said second channel means comprises the interior of said elongated tubular inner member.

5. A method of endoscopically resecting tissue in a gas filled body cavity comprising the steps of:

pressurizing said body cavity with gas and maintaining said gas at a predetermined pressure within said body cavity;

inserting into said body cavity a cutting means for resecting tissue, said cutting means having an aspirating lumen for aspirating resected tissue and gas;

resecting selected tissue in said body cavity;

aspirating the resected tissue and gas;

separating the resected tissue and gas to produce reusable gas;

returning said reusable gas to said body cavity.

6. A method according to claim 5 wherein said cutting means is a powered device having a movable elongated tubular cutting element adapted to move relative to a stationary elongated element and wherein said aspirating step comprises aspirating resected tissue and ambient gas through the interior of said tubular movable element.

* * * * *